United States Patent [19]

Nishidate et al.

[11] Patent Number: 5,492,815
[45] Date of Patent: Feb. 20, 1996

[54] METHOD OF DETERMINING GLUCOSE-6-PHOSPHATE AND COMPOSITION THEREFOR

[75] Inventors: Kazuyoshi Nishidate; Yoko Suzuki; Satoshi Inaba, all of Chiba, Japan

[73] Assignee: Iatron Laboratories, Inc., Tokyo, Japan

[21] Appl. No.: 187,800

[22] Filed: Jan. 26, 1994

Related U.S. Application Data

[63] Continuation of Ser. No. 768,695, Oct. 17, 1991, abandoned.

[30] Foreign Application Priority Data

Feb. 20, 1990  [JP]  Japan ........................ 2-39324

[51] Int. Cl.⁶ .................. C12Q 1/26; C12Q 1/32; G01N 33/00
[52] U.S. Cl. .................. 435/26; 435/25; 435/4; 435/22; 435/17; 435/14; 436/94; 436/95
[58] Field of Search ............... 435/26, 25, 190, 435/22, 874, 94, 14, 175, 7.1, 4, 22, 17; 436/15, 536, 177, 94, 95

[56] References Cited

U.S. PATENT DOCUMENTS

| | | | |
|---|---|---|---|
| 4,427,771 | 1/1984 | Misaki et al. | 435/26 |
| 4,438,199 | 3/1984 | Miwa et al. | 435/26 |
| 4,446,231 | 5/1984 | Self | 435/26 |
| 4,460,686 | 7/1984 | Hartmeier | 435/175 |
| 4,705,749 | 11/1987 | Willnow et al. | 435/15 |
| 5,066,582 | 11/1991 | Tsuruta et al. | 435/7.1 |
| 5,082,786 | 1/1992 | Nakamoto | 435/14 |
| 5,118,404 | 6/1992 | Saito | 435/14 |

OTHER PUBLICATIONS

Beutler et al; J. Lab. Clin Med., 107(6), 502–7.

Moir et al; Biochem. J. (1988) 256,69–73.

Primary Examiner—Michael G. Wityshyn
Assistant Examiner—Louise N. Leary
Attorney, Agent, or Firm—Burgess, Ryan & Wayne

[57] ABSTRACT

A method is provided for determining glucose-6-phosphate, including the step of dehydrogenating glucose-6-phosphate and NAD or NADP in the presence of glucose-6-phosphate dehydrogenase to produce 6-phosphogluconate and NADH or NADPH, wherein the determination is carried out in the presence of 6-phosphogluconolactonase. Also provided is a composition for determining glucose-6-phosphate, characterized by containing 6-phosphogluconolactonase, glucose-6-phosphate dehydrogenase, and NAD or NADP.

4 Claims, 3 Drawing Sheets

METHOD OF DETERMINING GLUCOSE-6-PHOSPHATE AND COMPOSITION THEREFOR

This application is a continuation of application Ser. No. 07/768,695, filed Oct. 17, 1991, now abandoned.

TECHNICAL FIELD

The present invention relates to a method and composition of determining glucose-6-phosphate.

In the present specification, the abbreviations used for nucleic acids, nucleotides, saccharides, enzymes, or the like are those based on recommendations of the Commission on Biological Nomenclature (CBN) or those in accordance with common use in the field, and specifically are as follows:

ADP: Adenosine diphosphate
AMY: Amylase
ATP: Adenosine triphosphate
CR: Creatine
CK: Creatine kinase
CMS: Carboxy methyl starch
CP: Creatine phosphate
GA: Glucoamylase
Glc: Glucose
Glck: Glucokinase
G6P: glucose-6-phosphate
G6PDH: Glucose-6-phosphate dehydrogenase
HK: Hexokinase
NAD: Oxidized type of nicotinamide adenine dinucleotide
NADH: Reduced type of nicotinamide adenine dinucleotide
NADP: Oxidized type of nicotinamide adenine dinucleotide phosphate
NADPH: Reduced type of nicotinamide adenine dinucleotide phosphate
6PG: 6-phosphogluconate
6PG-δ-L: 6-phospho-D-glucono-δ-lactone

BACKGROUND ART

Determination techniques are widely used to analyze various enzymes or physiologically active substances contained in biological liquid samples such as human sera, based on the specificity of enzyme reactions, and then make use of the results for diagnosis of diseases and clinical examinations. In these determination techniques, there is a well known method of determining various physiologically active substances, by quantitatively converting the physiologically active substances to be detected to glucose-6-phosphate (G6P), dehydrogenating the resulting glucose-6-phosphate (G6P) in the presence of glucose-6-phosphate dehydrogenase (G6PDH) and NAD or NADP to produce 6-phosphogluconate (6PG), as shown by the following reaction formula (I):

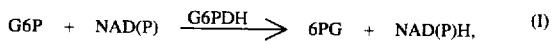

$$G6P + NAD(P) \xrightarrow{G6PDH} 6PG + NAD(P)H, \quad (I)$$

measuring the amount of the simultaneously produced NADH or NADPH by the absorbance thereof, and thus quantifying the physiologically active substances to be detected.

As physiologically active substances which can quantitatively be determined by converting to G6P, there may be mentioned, for example, creatine kinase (CK) which is the diagnostic indicator of cardiac infarction, muscular dystrophy, and the like; amylase (AMY) which serves as the diagnostic indicator of pancreatic disease, liver disease and the like; and glucose (Glc) which serves as the diagnostic indicator of diabetes and the like. It is possible to yield NAD(P)H by the reaction of the formula (I) from the quantitatively converted G6P, measure the increase of NAD(P)H, for example, from the change of absorbance at 340 nm, analyze the level of the physiologically active substances from the measured value, and thereby perform diagnosis of diseases and clinical examinations.

In the conventional determination systems, however, if the content of the physiologically active substances in the sample exceeded a certain amount, the amount of the NAD(P)H produced by a predetermined component ratio of a reagent used and within a predetermined reaction time would sometimes not increase quantitatively, and therefore it was not possible to accurately measure the content of the physiologically active substances. Therefore, when the initial measurement showed that a high content of the physiologically active substances was included in the sample, it was necessary to suitably dilute the sample and repeat the determination procedure.

The object of the present invention is to provide a means which enables accurate determination even in high concentration regions where accurate determination was not possible in the conventional methods.

DISCLOSURE OF INVENTION

The above-mentioned object of the present invention may be achieved by a method for determining glucose-6-phosphate, including the step of dehydrogenating glucose-6-phosphate and NAD or NADP in the presence of glucose-6-phosphate dehydrogenase to produce 6-phosphogluconate and NADH or NADPH, characterized in that the determination is carried out in the presence of 6-phosphogluconolactonase.

Further, the present invention relates to a composition for determining glucose-6-phosphate, characterized by containing 6-phosphogluconolactonase, glucose-6-phosphate dehydrogenase, and NAD or NADP.

BEST MODE FOR CARRYING OUT THE INVENTION

Figure 1:
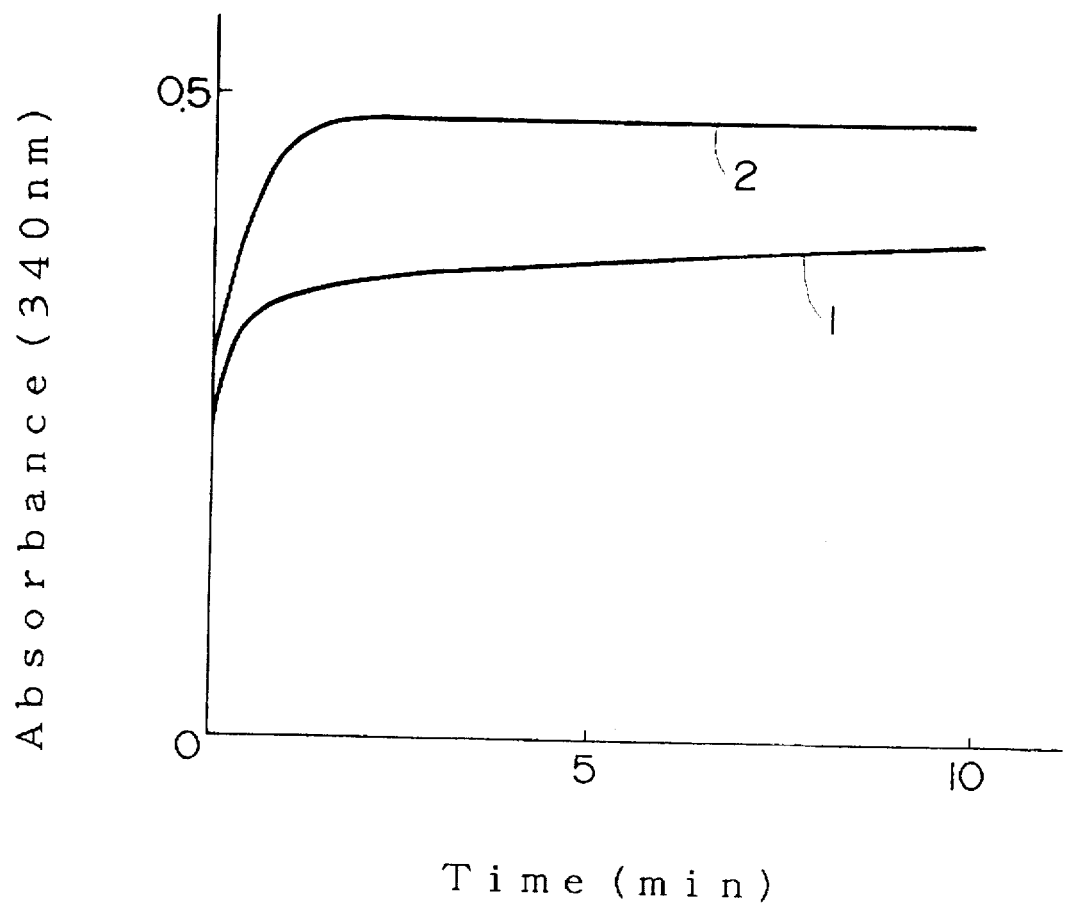
FIG. 1 is a graph showing the difference in the amounts of glucose-6-phosphate consumed in the presence (curve 2) and absence (curve 1) of 6-phosphogluconolactonase of the present invention.

The characteristic feature of the determination method and composition in accordance with the present invention resides in introduction of 6-phosphogluconolactonase into the conventional G6P determination system.

Therefore, the G6P converted from any known reaction system may be used in the present invention. For example, the G6P used in the present invention may be those converted in the determination of creatine kinase (CK), amylase (AMY), or glucose (Glc). Further, as the G6PDH, any enzymes (for example, a commercially available enzymes) used in the conventional methods may be used in the present invention.

The 6-phosphogluconolactonase newly added in the present invention is a known enzyme and has activity to change 6-phospho-D-glucono-δ-lactone (6PG-δ-L) to 6-phosphogluconate (6PG) as mentioned below, and is described, for example, in *J. Research Natl. Bur. Standards*, 48, 163 (1952) or *Seikagaku* (*Biochemistry*), 37, 788 (1965). The 6-phosphogluconolactonase may be obtained, for example, from microorganisms belonging to the Pseudomonas or Leuconostoc or from yeast. The amount of the 6-phospho-gluconolactonase added is not particularly limited. It is enough if the 6-phosphogluconolactonase is present in a sufficient amount so that the reaction from 6PG-δ-L to 6PG proceeds.

The analytical composition of the present invention contains 0.01 to 50 U/ml, preferably 0.01 to 10 U/ml of 6-phosphogluconolactonase, 0.5 to 20 U/ml, preferably 1 to 5 U/ml of glucose-6-phosphate dehydrogenase, and 0.2 to 20 mM, preferably 0.5 to 5 mM of NAD or NADP.

In the present invention, there may be used any buffer solutions which enable to adjust the determination system to be acidic or weakly alkaline (in particular, pH ca. 5.5 to ca. 8.5), for example, imidazole buffer solution, tris buffer solution, phosphate buffer solution, or Good's buffer solution.

In accordance with the present invention, the activity of the physiologically active substances to be detected can be determined by adding a reagent composition containing G6PDH, NAD(P) and 6-phosphogluconolactonase to the G6P converted from the physiologically active substances by various reaction systems (or making said reagent composition present in the reaction systems yielding the G6P from the beginning), and measuring the amount of NAD(P)H produced by the reaction by the absorbance in the vicinity of 340 nm to determine the activity of the physiologically active substances from the measured value.

Using the present invention, it is possible to determine the creatine kinase (CK), amylase (AMY), or glucose (Glc) contained in aqueous liquids, in particular biological aqueous liquids, for example, blood or liquids derived from blood (in particular, serum or plasma) or urine or tissue extracts. Methods for determining these physiologically active substances will be explained hereinafter.

CREATINE KINASE (CK)

An example of the reaction scheme of the known method for determining CK is as follows:

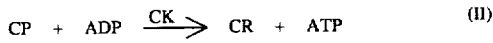

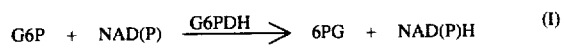

According to the present invention, 6-phosphogluconolactonase is made present in the dehydrogenation reaction of the above formula (I). The present invention may be carried out either by a one-step process or a multi-step process, each comprising the reaction steps of the above formula (II), formula (III), and formula (I). Therefore, the 6-phosphogluconolactonase may be present from the beginning in the reaction system or may be added later. In this method of determining CK, the sample to be detected is not limited, so long as there is a possibility of CK being present. In particular, there may be mentioned blood or liquids derived from blood (in particular, serum or plasma) or urine or tissue extracts.

AMYLASE (AMY)

An example of the reaction scheme of the known method for determining AMY is as follows:

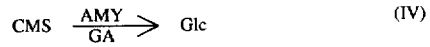

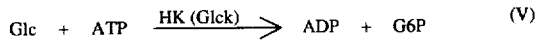

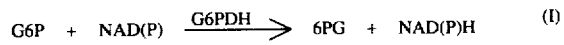

According to the present invention, 6-phosphogluconolactonase is made present in the dehydrogenation reaction of the above formula (I). The present invention may be carried out either by a one-step process or a multi-step process, each comprising the reaction steps of the above formula (IV), formula (V), and formula (I). Therefore, the 6-phosphogluconolactonase may be present from the beginning in the reaction system or may be added later. In this method of determining AMY, the sample to be detected is not limited, so long as there is a possibility of AMY being continaied. In particular, there may be mentioned blood or liquids derived from blood (in particular, serum or plasma) or urine or tissue extracts.

GLUCOSE (Glc)

An example of the reaction scheme of the known method for determining Glc is as follows:

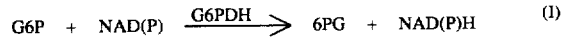

According to the present invention, 6-phosphogluconolactonase is made present in the dehydrogenation reaction of the above formula (I). The present invention may be carried out either by a one-step process or a multi-step process, each comprising the reaction steps of the above formula (VI) and formula (I). Therefore, the 6-phosphogluconolactonase may be present from the beginning in the reaction system or may be added later. In this method of determining Glc, the sample to be detected is not limited, so long as there is a possibility of Glc being present. In particular, there may be mentioned blood or liquids derived from blood (in particular, serum or plasma) or urine or tissue extracts.

An explanation will be made of the principle of determination in the present invention, but the present invention is not limited by the following descriptions.

The reaction of the formula (I) can be divided into elementary reactions as follows:

-continued

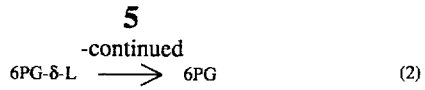
(2)

As above, when dehydrogenation of glucose-6-phosphate (G6P) is carried out in the presence of glucose-6-phosphate dehydrogenase (G6PDH), the first product is 6-phospho-D-glucono-δ-lactone (6PG-δ-L), and thereafter, 6-phosphogluconate (6PG) is produced.

It is believed that the reaction of the formula (1) is reversible, while the reaction of the formula (2) is irreversible. If the reaction rate of the formula (2) is higher than that of the reaction of the formula (1) in the left direction (reaction from 6PG-δ-L to G6P), the reaction product of the formula (1), that is, 6PG-δ-L will immediately be converted to 6PG by the reaction of the formula (2), and so the reaction of the formula (1) progresses in the right direction (from G6P to 6PG-δ-L) and therefore, the amount of NAD(P)H in the reaction system increases. To the contrary, if the reaction rate of the formula (2) is lower, the reaction product of the formula (1), that is, 6PG-δ-L, will return to G6P by the reversible reaction of the formula (1), and at the same time, the NAD(P)H will be consumed. Therefore, the above reaction would suppress the increase of NAD(P)H in the reaction system.

In the past, it was considered that the reaction of the formula (2) did not particularly require any enzyme and that the reaction proceeded rapidly, for example, by hydrolysis etc.

However, the present inventors found that when 6-phosphogluconolactonase according to the present invention is absent, the reaction rate of the formula (2) is extremely slow at pH of 8.5 or less, although the reaction of the formula (2) proceeds relatively quickly at pH of 8.5 or more.

Therefore, if the reaction of the above-mentioned formula (I), that is, the formula (1) and the formula (2), is carried out in the absence of the 6-phosphogluconolactonase according to the present invention at pH of 8.5 or less, the reaction will not be completed within the normal measuring time and the results obtained will be inaccurate. For example, the optimum pH for determining the activity of creatine kinase (CK) is generally about 6.5, so the above phenomenon may considerably affect the result.

In accordance with the present invention, as mentioned above, it is possible to obtain more rapid, accurate, and highly precise determination results by introducing a particular enzyme into the hydrogenation reaction process of the above formula (I) so as to promote the reaction of the formula (2) and complete the reaction in a short time.

It is to be understood that the present invention is particularly preferable for use in determination at pH of 8.5 or less, but when used in determination at pH of 8.5 or more, it is possible to obtain even more rapid, preciser, and accurate determination results.

EXAMPLES

The present invention will be concretely explained by Examples hereinafter, but these Examples are not intended to limit the scope of the invention in any manner.

EXAMPLE 1

Three milliliters of a 100 mM imidazole acetate buffer solution (pH=6.7) containing 2 U/ml of G6PDH (Boehringer-Mannheim Gmbh) and 2.5 mM NADP (Oriental Yeast Co.) (hereinafter referred to as the solution A) were mixed with 30 μl of a 100 mM imidazole buffer solution (pH=6.7) containing 8 mM G6P (Oriental Yeast Co.). The mixture was reacted at 37° C. and the changes of absorbance at 340 nm, indicating the increase of NADPH, were measured continuously for 10 minutes. The results are shown by curve 1 in FIG. 1.

The same procedure was repeated, except that instead of the solution A, 3 ml of a solution prepared by adding to the solution A 0.2 U/ml of 6-phosphogluconolactonase (prepared in Reference Example as mentioned below) was used. The increase of NADPH was measured for 10 minutes. The results are shown by curve 2 in FIG. 1.

EXAMPLE 2

CK (derived from rabbit muscle: Boehringer-Mannheim Gmbh) was added at a concentration of 5,000 U/l to human pooled serum. Then, the serum containing CK was diluted by purified water to prepare a series of 10 dilutions (500 U/l, 1,000 U/l, 1,500 U/l, 2,000 U/l, 2,500 U/l, 3,000 U/l, 3,500 U/l, 4,000 U/l, 4,500 U/l, and 5,000 U/l).

Figure 2:
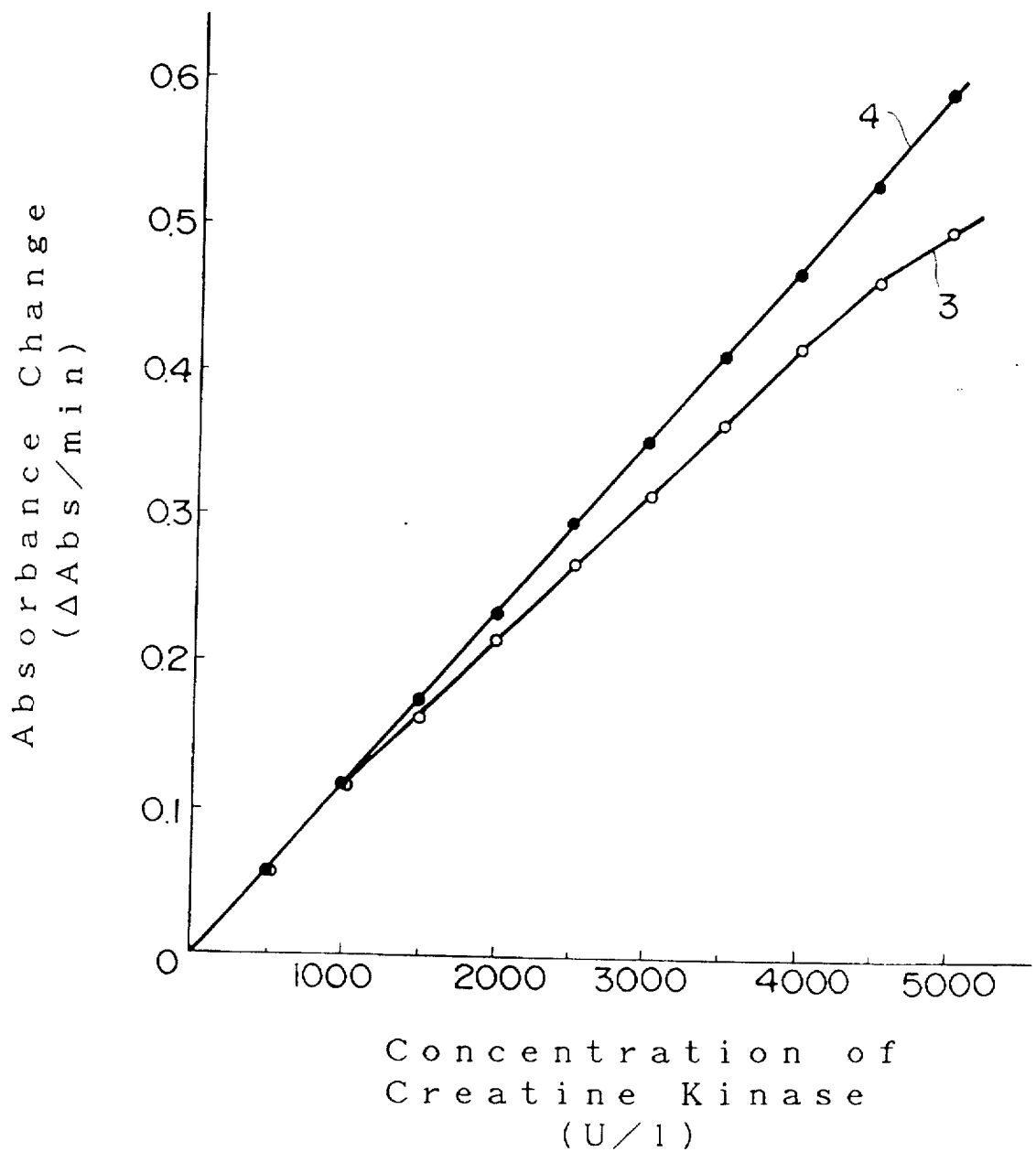
FIG. 2 is a graph showing the difference in the amounts of creatine consumed in the presence (curve 4) and absence (curve 3) of 6-phosphogluconolactonase of the present invention.

Eight microliters of the above-mentioned dilution series were mixed with 320 μl of 100 mM imidazole acetate solution (pH=6.7) containing 4 U/ml of glucokinase (Unitika), 25 mM glucose, 2 mM ADP, 1.5 U/ml of G6PDH (Boehringer-Mannheim Gmbh) and 2.8 mM NADP (Oriental Yeast Co.) (hereinafter referred to as solution B) and 80 μl of 25 mM tris hydrochloride buffer solution (pH=7.5) containing 125 mM creatine phosphate and 50 mM magnesium acetate. The mixture was reacted at 37° C. Then, the changes of absorbance at 340 nm were measured from 3 to 5 minutes after the reaction begun, to find the change in absorbance per unit time (ΔAbs/min). The results are shown by the open circles (line 3) in FIG. 2.

The same procedure was repeated, except that instead of the above solution B, 320 μl of a solution prepared by adding to the solution B 0.2 U/ml of 6-phosphogluconolactonase (prepared by Reference Example as mentioned below) was used. The amount of NADPH was measured. The results are shown by the closed circles (line 4) in FIG. 2.

EXAMPLE 3

By diluting glucose with purified water, diluted solutions having the concentrations of 400 mg/dl, 700 mg/dl and 1,000 mg/dl of glucose were prepared.

Two milliliters of 100 mM imidazole acetate solution (pH=6.5) containing 4 U/ml of glucokinase (Unitika), 1.5 U/ml of G6PDH (Boehringer-Mannheim Gmbh) and 2.8 mM NADP (Oriental Yeast Co.) (hereinafter referred to as solution C) were mixed with 0.50 ml of 100 mM imidazole acetate solution (pH=6.5) containing 8.5 mM ATP (Boehringer-Mannheim Gmbh), and thereafter, 20 μl of the diluted glucose solutions were added, respectively. The mixture was reacted at 37° C. Then, the changes of absorbance at 340 nm were measured continuously for 10 minutes after the reaction begun.

The same procedure was repeated, except that instead of the above solution C, a solution prepared by adding 6-phosphogluconolactonase (prepared by Reference Example as mentioned below) to the solution C so that the concentration thereof is 0.09 U/ml was used. The amount of NADPH was measured.

Figure 3:
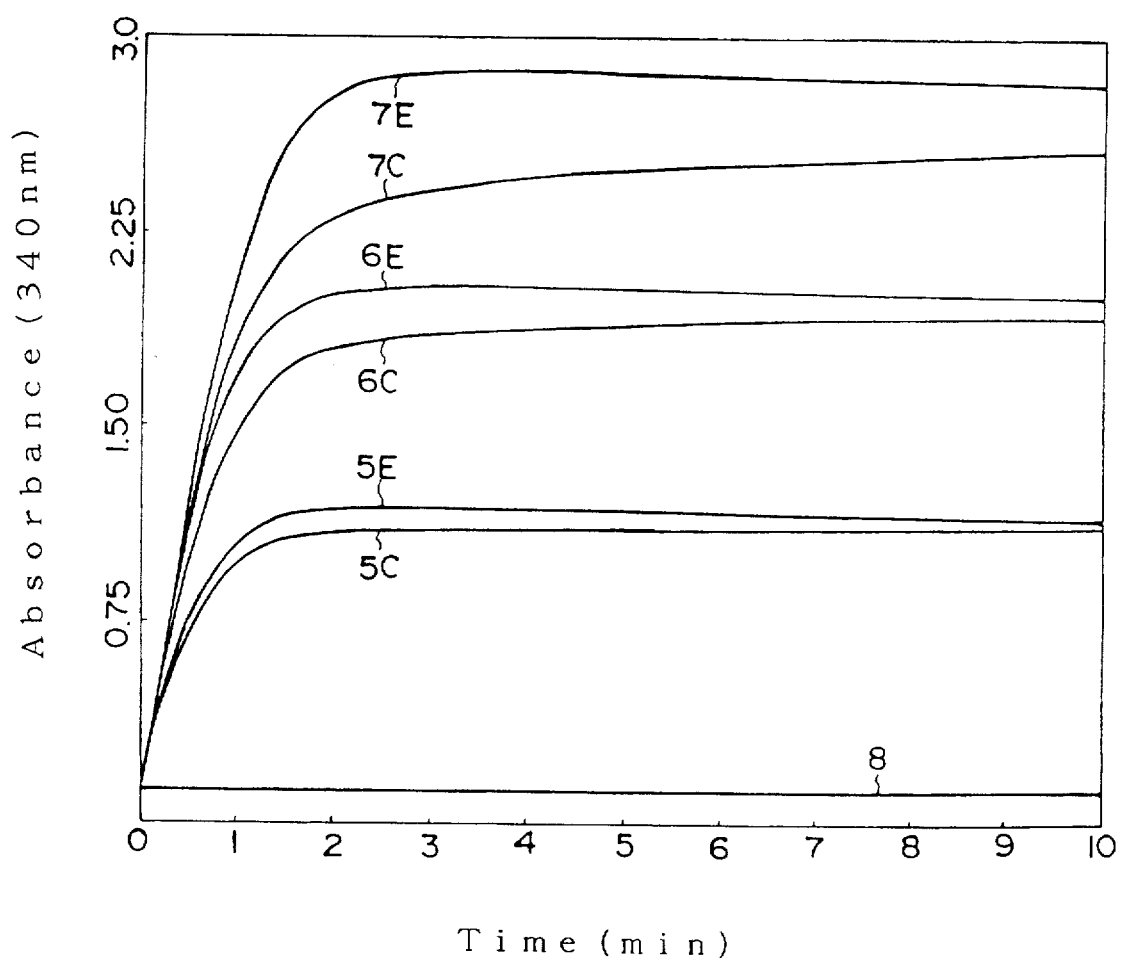
FIG. 3 is a graph showing the difference in the amounts of glucose consumed in the presence and absence of 6-phosphogluconolactonase of the present invention.

The results are shown in FIG. 3. In FIG. 3, the curve 5C denotes the case wherein 6-phosphogluconolactonase was not added to the diluted solution containing 400 mg/dl of glucose, the curve 5E denotes the case wherein 6-phosphogluconolactonase was added to the diluted solution containing 400 mg/dl of glucose, the curve 6C denotes the case wherein 6-phosphogluconolactonase was not added to the diluted solution containing 700 mg/dl of glucose, the curve 6E denotes the case wherein 6-phosphogluconolactonase was added to the diluted solution containing 700 mg/dl of glucose, the curve 7C denotes the case wherein 6-phosphogluconolactonase was not added to the diluted solution containing 1,000 mg/dl of glucose, the curve 7E denotes the case wherein 6-phosphogluconolactonase was added to the diluted solution containing 1,000 mg/dl of glucose, and the curve 8 denotes the case wherein 6-phosphogluconolactonase was added to purified water not containing glucose.

REFERENCE EXAMPLE

Preparation of 6-phosphogluconolactonase (1) Using Penassay broth (Difco Co.), *Pseudmonas fluorescens* (RIMD 1615005; obtained from Osaka University, Research Institute for Microbial Disease) was cultivated at 30° C. for one day. The cultivated medium was inoculated for one day at 30° C. in a heart infusion medium. The resulting incubated liquid was centrifuged to harvest the cells. The cells were washed with physiological water, destroyed by sonication in a tris buffer solution, and further centrifuged. The supernatant was fractionated by ammonium sulfate at pH of 7.5, and the proteinous component which precipitated at a 30 to 70 percent saturation was centrifuged and collected. The proteinous component was dissolved in a tris buffer solution and dialyzed, then roughly purified by a DEAE-cellulose column. The resulting crude product was further purified by HPLC [packed material: ZORBAX GF-250 (Du Pont)], then the desired 6-phosphogluconolactonase was isolated as a single peak fraction eluted at a molecular weight of 30,000 to 50,000.

(2) The activity of the isolated 6-phosphogluconolactonase was determined by the following test:

Solutions Used

Solution D: Prepared by employing a 100 mM imidazole acetate buffer solution (pH=6.5) containing 10 mM magnesium chloride so as to contain 0.85 mM NADP and 0.08 mM G6P.

Solution E: Prepared by dissolving G6PDH (not containing 6-phosphogluconolactonase) in purified water at a concentration of 200 U/ml.

Solution F: An ammonium sulfate suspension of 6-PGDH (120 U/ml: Boehringer-Mannheim Gmbh)

Procedure

The solution D (3 ml) was added to the solution E (10 μl), and the reaction was carried out at 37° C. for 2 minutes. After adding 20 μl of 6-phosphogluconolactonase solution prepared in Reference Example (1), the whole was allowed to stand at 37° C. for 2 minutes, and then, 5 μl of the solution F was added. Then, the changes of absorbances at 340 nm were measured from 2 to 4 minutes after the addition of the solution F.

In the test, when the absorbance 2 to 4 minutes later exceeds 0.06 Abs., or when the absorbance before 2 minutes elapse exceeds 0.8 Abs., measurement was carried out again after diluting 6-phosphogluconolactonase with purified water.

Control tests were carried out, using purified water instead of 6-phosphogluconolactonase solution.

The activity was calculated by the following equation:

Activity of 6-phosphogluconolactonase (U/ml) =

$$\frac{\Delta E/T}{\epsilon \times d} \times \frac{V}{v} \times DF$$

wherein $\Delta E$ denotes a change of absorbance, T denotes a reaction time (min), $\epsilon$ denotes an absorbancy index of NADPH (6.22 cm$^2$/μmol), d denotes a length of a cell (cm), V denotes a final liquid amount (ml), v denote an amount of the liquid containing 6-phosphogluconolactonase (ml), and DF denotes a dilution ratio of the liquid containing 6-phosphogluconolactonase.

INDUSTRY APPLICABILITY

In accordance with the present invention, it is possible to carry out more rapid, more accurate, and preciser determination by introducing 6-phosphogluconolactonase in the dehydrogenation reaction process which yields 6-phosphogluconate (6PG) from glucose-6-phosphate (G6P), to promote the reaction from G6P to 6PG.

Therefore, it is possible to rapidly, precisely and accurately analyze the level of physiologically active substances included in various biological samples, for example, creatine kinase (CK) which is the diagnostic indicator of cardiac infarction, muscular dystrophy, and the like, amylase (AMY) which serves as the diagnostic indicator of pancreatic disease, liver disease and the like, or glucose (Glc) which serves as the diagnostic indicator of diabetes and the like, by quantitatively converting G6P from the physiologically active substances to yield NAD(P)H, and measuring the amount thereof, whereby diagnosis of diseases and clinical examinations can be carried out.

We claim:

1. In a method for quantitatively determining a physiologically active substance capable of producing glucose-6-phosphate in a sample, comprising the steps of:

(I) bringing said sample into contact with a composition of (i) one or more enzymes and reagents capable of quantitatively producing glucose-6-phosphate from said physiologically active substance, (ii) glucose-6-phosphate dehydrogenase and (iii) NAD or NADP, to thereby effect in the presence of said physiologically active substance, an ordered sequence of reactions wherein (a) glucose-6-phosphate is quantitatively produced from said physiologically active substance; and, (b) glucose-6-phosphate and NAD or NADP are converted to 6-phosphogluconate and NADH or NADPH; and then, (II) quantitatively detecting NADH or NADPH produced in said step (I)(b), the improvement which comprises adding to said composition from 0.1 to 50 u/ml of 6-phosphogluconolactonase to accelerate the conversion of glucose-6-phosphate and NAD or NADP to 6-phosphogluconate and NADH or NADPH in the reaction (b) whereby the accuracy for determining said physiological active substance is optimized by the presence of 6-phosphogluconolactonase whereby a linear relationship of the absorbance of said NADH or NADPH to the concentration of said substance is maintained.

2. The method according to claim 1, wherein said physiologically active substance is creatine kinase, and said one or more enzymes and reagents are creatine phosphate, glucose, hexokinase and ADP.

3. The method according to claim 1, wherein said physiologically active substance is amylase, and said one or more enzymes and reagents are starch, glucoamylase, hexokinase and ATP.

4. The method according to claim 1, wherein said physiologically active substance is glucose, and said one or more enzymes and reagents are hexokinase and ATP.

* * * * *

UNITED STATES PATENT AND TRADEMARK OFFICE
CERTIFICATE OF CORRECTION

PATENT NO. : 5,492,815
DATED : February 20, 1996
INVENTOR(S) : Kazuyoshi Nishidate, et al.

It is certified that error appears in the above-indentified patent and that said Letters Patent is hereby corrected as shown below:

Claim 1, line 3 of paragraph (II): change "0.1" to read --0.01--.

Signed and Sealed this

Third Day of June, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,492,815
DATED : February 20, 1996
INVENTOR(S) : Kazuyoshi Nishidate, et. al.

It is certified that error appears in the above-indentified patent and that said Letters Patent is hereby corrected as shown below:

Title page, item [73], Assignee: should read--Iatron Laboratories, Inc., and Unitika Ltd., Tokyo, Japan--.

Signed and Sealed this

Twenty-sixth Day of August, 1997

BRUCE LEHMAN

Attest:

Attesting Officer

Commissioner of Patents and Trademarks